(12) United States Patent
Park et al.

(10) Patent No.: US 11,584,749 B2
(45) Date of Patent: Feb. 21, 2023

(54) PHOSPHOR-TETRAZINE COMPOUND AND USE THEREOF

(71) Applicants: Spark Biopharma, Inc., Seoul (KR); Seoul National University R&DB Foundation, Seoul (KR)

(72) Inventors: Seung Bum Park, Seoul (KR); Young Jun Lee, Seoul (KR)

(73) Assignees: Spark Biopharma, Inc., Seoul (KR); Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 17/058,893

(22) PCT Filed: May 31, 2018

(86) PCT No.: PCT/KR2018/006206
§ 371 (c)(1),
(2) Date: Nov. 25, 2020

(87) PCT Pub. No.: WO2019/231016
PCT Pub. Date: Dec. 5, 2019

(65) Prior Publication Data
US 2021/0198260 A1   Jul. 1, 2021

(51) Int. Cl.
*C07D 471/14* (2006.01)
*G01N 33/52* (2006.01)

(52) U.S. Cl.
CPC ........... *C07D 471/14* (2013.01); *G01N 33/52* (2013.01)

(58) Field of Classification Search
CPC .............................. C07D 471/14; A61K 49/00
USPC ........................................................ 544/179
See application file for complete search history.

(56) References Cited

U.S. PATENT DOCUMENTS

2009/0023916 A1   1/2009   Fox et al.

FOREIGN PATENT DOCUMENTS

| JP | 5993940 B2 | 9/2016 |
|---|---|---|
| KR | 20090114092 A | 11/2009 |
| KR | 10-20130025709 A | 3/2013 |

OTHER PUBLICATIONS

Lee, Y. et al., "Systematic Exploration of Indolizine- Based Small Fluorescent Molecules," Doctoral Thesis in Organic Chemistry, Department of Chemisry, Graduate School of Seoul National University, May 14, 2018, 252 pages.
Choi, E. J. et al., "Rational Perturbation of the Fluorescence Quantum Yield in Emission-Tunable and Predictable Fluorophores (Seoul-Fluors) by a Facile Synthetic Method Involving C—H Activation," Angewandte Chemie International Edition, vol. 53:1346-1350 (2014).
Lee, Y. et al.,"Monochromophoric Design Strategy for Tetrazine-Based Colorful Bioorthogonal Probes with a Single Fluorescent Core Skeleton," Journal of the American Chemical Society, vol. 140:974-983 (2018).
Lee, Y. et al.,"Tetrazine-Containing Colorful Bioorthogonal Probes based on the Indolizine Core Skeleton," 121th General Meeting of Korean Chemical Society. Apr. 19, 2018, ICC Jeju, ORGN.O-8 See abstract, 4 pages.
Park, J-W et al., "Measurement of Lipid Droplet Accumulation Kinetics Chlamydomonas reinhardtii Using Seoul-Fluor," Energies, vol. 6:5703-5716; doi:10.3390/en6115703 (2013).
Choi, E.J., et al., "Unique photophysical properties of 9-styryl-1,2-dihydropyrrolo[3,4-?]indolizin-3-one and its e?cient synthesis via direct C—H activation," Organic & Biomolecular Chemistry, vol. 13 (5202) 7 pages (2015).
Development for Technology of High Efficiency Fluorescence Enhancement in Vivo Probe, BRIC Trend, BRIC, Retrieved from the Internet <http://www.ibric.org/mybroad/read.php?Board=new&id=291143> See the entire document. Feb. 5, 2018.

*Primary Examiner* — Charanjit Aulakh
(74) *Attorney, Agent, or Firm* — United One Law Group LLC; Kongsik Kim; Jhongwoo Peck

(57) ABSTRACT

The present invention relates to a novel phosphor-tetrazine and a use thereof and, more particularly, provides a novel compound having high fluorescence amplification efficiency in various wavelength ranges by using a compound having a novel core skeleton called tert-butyl (3-(7-(6-methyl-1,2,4,5-tetrazin-3-yl)-3-oxo-9-phenyl-1H-pyrrolo[3,4-b]indolizin-2(3H)-yl)propyl)carbamate.

7 Claims, 4 Drawing Sheets

Example 1

Example 2

Example 3

Example 4

Comparative Example 1

Comparative Example 2

Comparative Example 3

Comparative Example 4

Example 1

Example 2

Example 3

Example 4

Comparative Example 1

Comparative Example 2

Comparative Example 3

Comparative Example 4

PHOSPHOR-TETRAZINE COMPOUND AND USE THEREOF

CROSS-REFERENCES TO RELATED APPLICATIONS

This application is a National Stage Entry of International Application PCT/KR2018/006206 filed on May 31, 2018. The aforementioned patent application is incorporated herein by reference in its entirety.

TECHNICAL FIELD

The present invention relates to a novel phosphor-tetrazine and a use thereof and, more particularly, provides a novel compound having high fluorescence amplification efficiency in various wavelength ranges by using a compound having a novel core skeleton called tert-butyl (3-(7-(6-methyl-1,2,4,5-tetrazin-3-yl)-3-oxo-9-phenyl-1H-pyrrolo[3,4-b]indolizin-2(3H)-yl)propyl)carbamate.

BACKGROUND ART

Fluorogenic probes have been widely used as research tools in biological science, clinical diagnosis and new drug development and the like due to their high sensitivity and ease of handling.

Bio-imaging, especially imaging in living cells plays an important role in studying life phenomena. The success or failure of such bio-imaging may depend on the development of a good fluorogenic probe. Therefore, a fluorogenic bioorthogonal probe that reacts with a desired target substance in living cells to fluoresce becomes a key element of bio-imaging.

In particular, a fluorogenic probe bound to tetrazine has been actively studied because it has rapid reactivity and high fluorescence amplification efficiency. However, the conventional tetrazine-based fluorogenic probe has a limitation in that the fluorescence amplification efficiency significantly decreases in a long wavelength range (>600 nm), which is known to have excellent light transmittance in vivo and little signal overlap with a biopolymer. This was a limiting factor that made it difficult to perform multiplex imaging for obtaining various informations in bio-imaging.

The conventional tetrazine-based fluorogenic probes induced quenching of the probe through an energy transfer method in which the excited energy of the fluorescent molecule is transferred to the tetrazine molecule, which is a quencher. Tetrazine is a quencher that fits well with a short wavelength fluorogenic probe, but a long wavelength fluorogenic probe does not fit well with tetrazine, so energy transfer is not smooth, and as a result, there is a limitation in which the fluorescence amplification efficiency is significantly reduced at a long wavelength. Therefore, the present inventor has attempted to develop a fluorogenic bioorthogonal probe having high fluorescence amplification efficiency regardless of the wavelength range.

DETAILED DESCRIPTION OF THE INVENTION

Technical Problem

The previously developed fluorogenic bioorthogonal probe electronically separates the fluorescent molecule from the tetrazine, and then induced the quenching of the probe through an energy transfer method in which the excited energy of the fluorescent molecule is transferred to the tetrazine molecule, a quencher. The above probe has the disadvantage that the fluorescence amplification efficiency is greatly reduced in a long wavelength range, but it is a method used by many researchers because it is easy to synthesize.

Therefore, an object of the present invention is to provide a fluorogenic probe having excellent fluorescence amplification efficiency even in a long wavelength range and a method of preparing the same.

Solution to Problem

In order to achieve the above object, the present invention provides a novel compound represented by Formula 1 below.

[Formula 1]

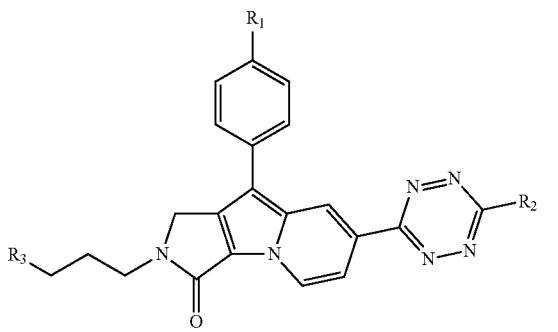

in which, $R_1$ is hydrogen, $C_1$-$C_6$ alkoxy, hydroxy or $NR_4R_5$ (wherein, $R_4$ and $R_5$ are each independently hydrogen, a $C_1$-$C_6$ alkyl group or a $C_3$-$C_8$ cycloalkyl group), $R_2$ is hydrogen, a $C_1$-$C_6$ alkyl, $C_6$-$C_{20}$ aryl or $C_4$-$C_{20}$ heteroaryl group, and $R_3$ is hydrogen, hydroxy, an alcohol protected by triisopropylsilyl (TIPS), a $C_3$-$C_8$ heterocyclic or amine group, wherein the heterocyclic or amine group may or may not be substituted with $C_1$-$C_6$ alkyl; a carboxyl$C_1$-$C_6$alkyl or tert-butyloxycarbonyl group (Boc group).

In addition, the present invention provides the compound characterized in that $R_1$ is hydrogen, $C_1$-$C_6$ alkoxy, or $NR_4R_5$ (wherein, $R_4$ and $R_5$ are each independently hydrogen or a $C_1$-$C_6$ alkyl group), $R_2$ is hydrogen or $C_1$-$C_6$ alkyl, and $R_3$ is hydrogen, a $C_3$-$C_8$ heterocyclic or amine group, wherein the heterocyclic or amine group may or may not be substituted with $C_1$-$C_6$ alkyl; a carboxyl$C_1$-$C_6$alkyl or tert-butyloxycarbonyl group (Boc group).

In addition, the present invention provides the compound characterized in that $R_2$ is $C_1$-$C_6$ alkyl.

In addition, the present invention provides the compound selected from the group consisting of compounds of Formulae 2 to 7 below:
[Formula 2]
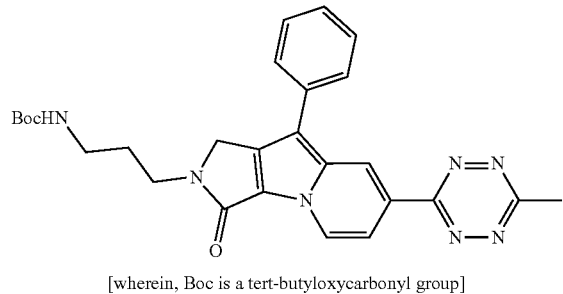
[wherein, Boc is a tert-butyloxycarbonyl group]
[Formula 3]
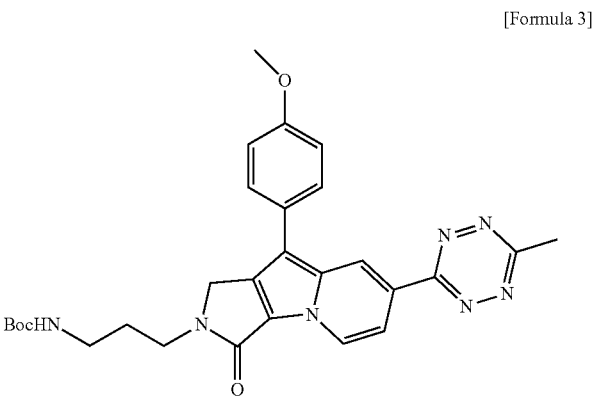
[Formula 4]
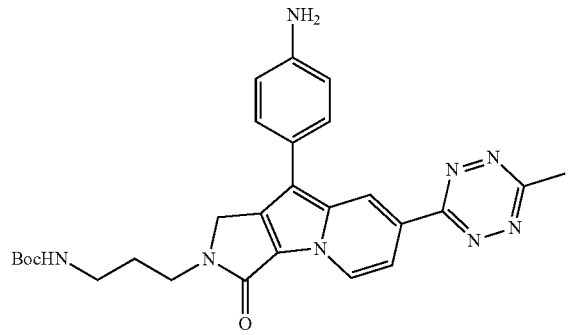
[Formula 5]
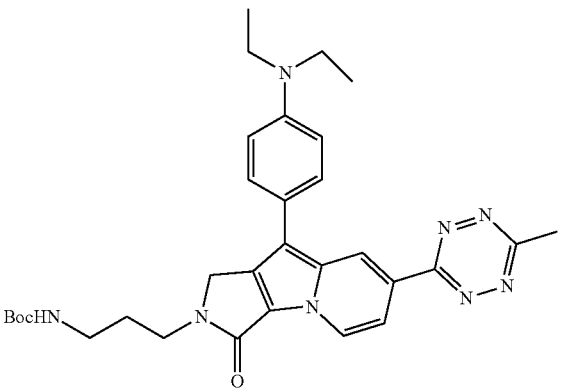
[Formula 6]
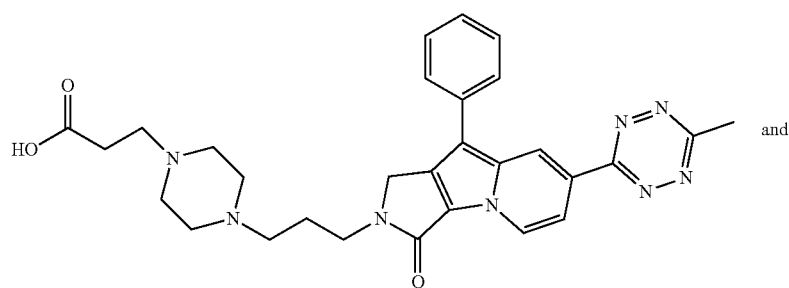
and
[Formula 7]
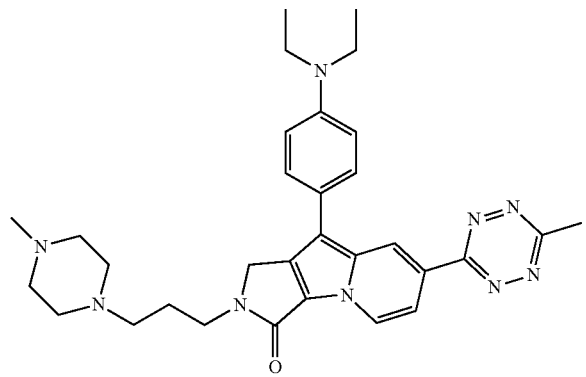

In addition, the present invention provides the compound characterized in that the compound does not have an absorption peak of 500-550 nm in the absorption spectrum measured using a UV-VIS spectrophotometer.

Effect of the Invention

The present invention provides a novel fluorogenic bioorthogonal probe capable of amplifying a fluorescence signal with very high efficiency in all wavelength ranges since it is possible to quench the excited energy of the phosphor regardless of the wavelength by treating the phosphor and the tetrazine quencher in a monochromophore type, with deviating from the conventional method of connecting the phosphor-tetrazine in a bichromophore type.

BEST MODE FOR CARRYING OUT THE INVENTION

Figure 1:
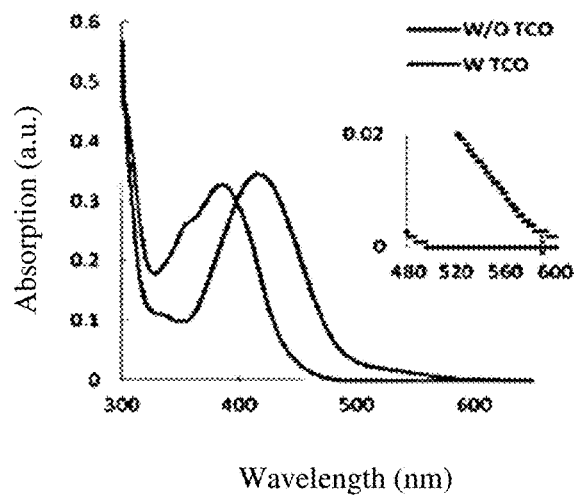
FIG. 1 shows the change in absorbance before and after the reaction between the compounds of Examples 1 to 4 and TCO.
Figure 1:
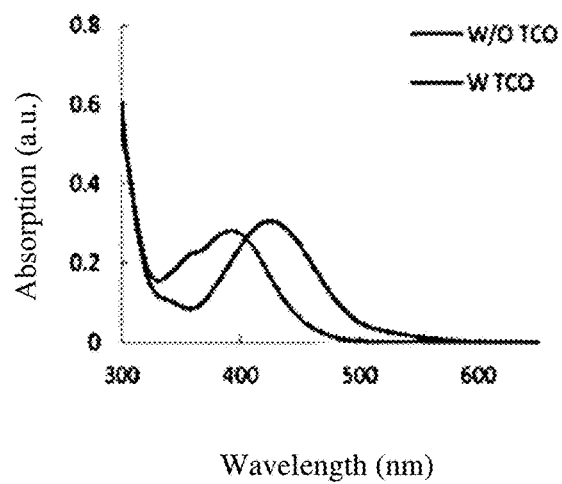
Figure 1:
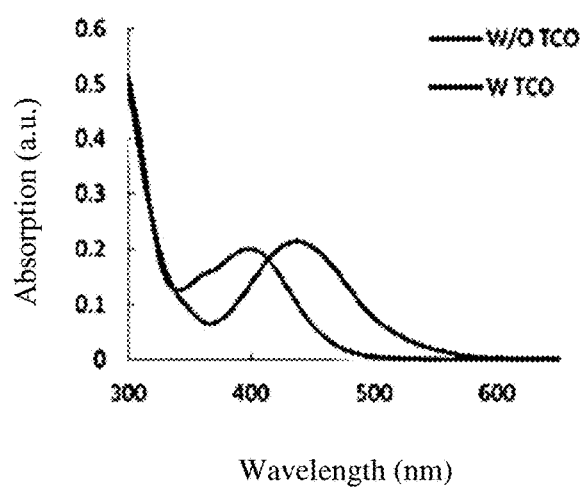
Figure 1:
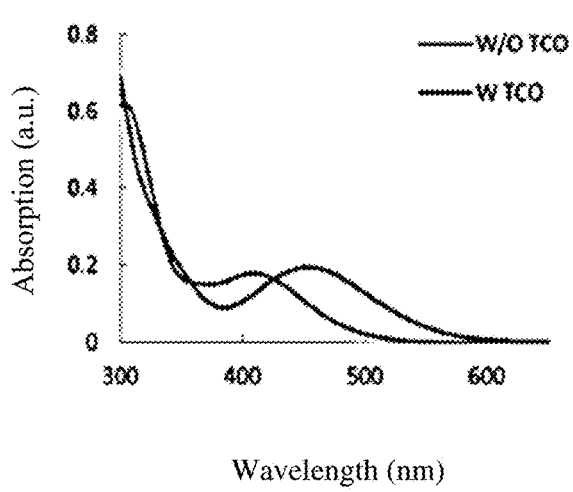

The present invention provides a novel compound represented by Formula 1 below.

The compound of the present invention is a compound having a core skeleton of "9-phenyl-2-propyl-7-(1,2,4,5-tetrazin-3-yl)-1H-pyrrolo[3,4-b](2H)-one" in Formula 1 above and a derivative thereof, and has special photophysical properties and photochemical properties through a change in a substituent group.

Specifically, the compound of the present invention enables tuning and prediction of a fluorescence wavelength through a change in a substituent group, thereby providing a new fluorogenic bioorthogonal probe that can be used at various wavelengths. In particular, it can be used as a useful fluorescent compound that can selectively track in vivo targets that have been difficult to observe due to a small amount of fluorescence expression.

Therefore, the compound of the present invention can be usefully used in organic light emitting elements, bio-imaging and bio applications as a fluorescent dye or a fluorogenic probe, and in particular, can be used as a fluorogenic probe capable of specifically labeling a protein of interest in the field of immunocytochemistry.

In Formula 1 above, $R_1$ is hydrogen, $C_1$-$C_6$ alkoxy, hydroxy or $NR_4R_5$ (wherein, $R_4$ and $R_5$ are each independently hydrogen, a $C_1$-$C_6$ alkyl group or a $C_3$-$C_8$ cycloalkyl group), $R_2$ is hydrogen, a $C_1$-$C_6$ alkyl, $C_6$-$C_{20}$ aryl or $C_4$-$C_{20}$ heteroaryl group, and $R_3$ is hydrogen, hydroxy, an alcohol protected by triisopropylsilyl (TIPS), a $C_3$-$C_8$ heterocyclic or amine group, wherein the heterocyclic or amine group may or may not be substituted with $C_1$-$C_6$ alkyl; a carboxyl$C_1$-$C_6$alkyl or tert-butyloxycarbonyl group (Boc group).

In addition, the present invention provides the compound characterized in that $R_1$ is hydrogen, $C_1$-$C_6$ alkoxy, or $NR_4R_5$ (wherein, $R_4$ and $R_5$ are each independently hydrogen or a $C_1$-$C_6$ alkyl group), $R_2$ is hydrogen or $C_1$-$C_6$ alkyl, and $R_3$ is hydrogen, a $C_3$-$C_8$ heterocyclic or amine group, wherein the heterocyclic or amine group may or may not be substituted with $C_1$-$C_6$ alkyl; a carboxyl$C_1$-$C_6$alkyl or tert-butyloxycarbonyl group (Boc group).

In addition, the present invention provides the compound characterized in that $R_2$ is $C_1$-$C_6$ alkyl.

In addition, the present invention provides the compound selected from the group consisting of compounds of Formulae 2 to 7 below:

[Formula 1]

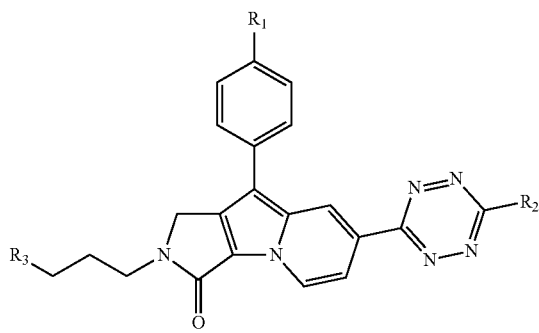

[Formula 2]

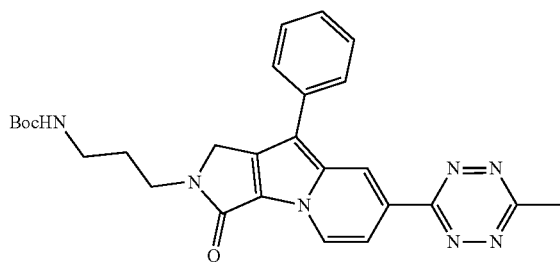

[wherein, Boc is a tert-butyloxycarbonyl group]

[Formula 3]

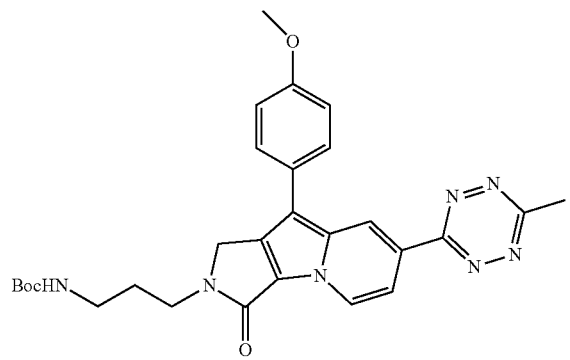

-continued

[Formula 4]

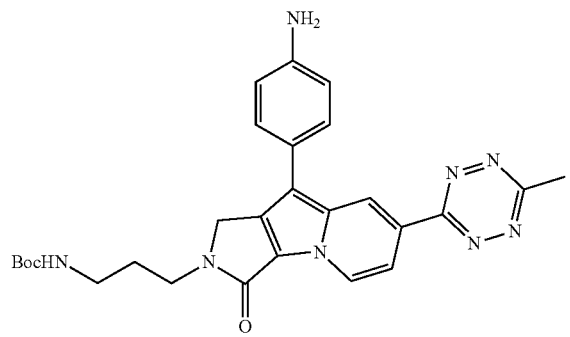

[Formula 5]

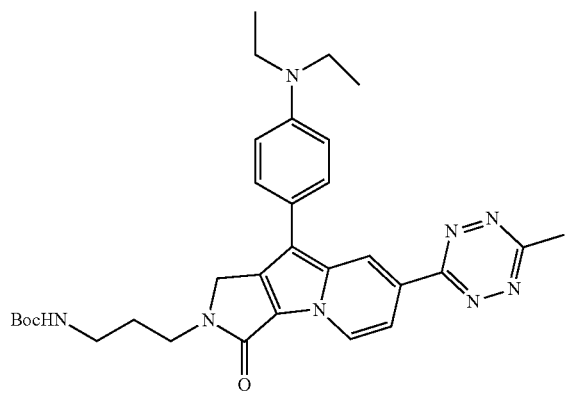

[Formula 6]

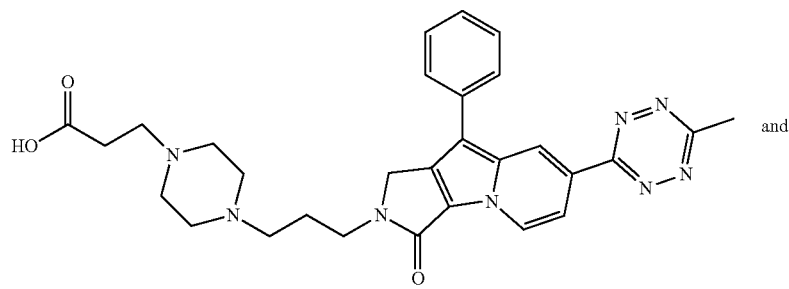

and

[Formula 7]

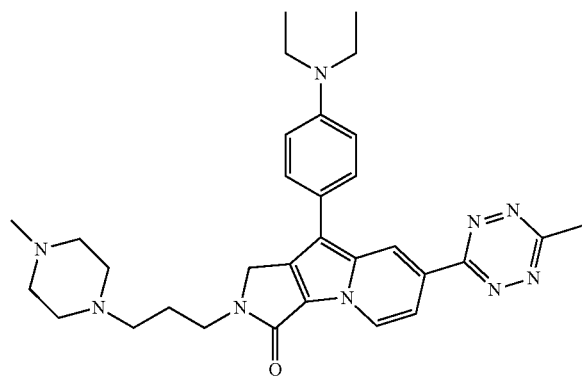

In addition, the present invention provides the compound characterized in that the compound does not have an absorption peak of 500-550 nm in the absorption spectrum measured using a UV-VIS spectrophotometer.

"Heterocyclic" is a heterocyclic having 3 to 30 ring atoms in which one or more ring carbons are each replaced with a heteroatom selected from B, N, O and S.

"Heteroaryl" is a heteroaryl having 3 to 30 ring atoms in which one or more ring carbons are each replaced with a heteroatom selected from B, N, O and S.

"Tetrazine" is an aromatic hexagonal ring compound containing four nitrogen atoms, and has a chemical reactivity that can cause a rapid biorthogonal reaction with a target substance, and can serve as a fluorescence quencher that reduces the fluorescence signal when connected to a fluorescent molecule. In addition, when tetrazine rapidly causes a chemical reaction with the target substance and the chemical structure is modified, the fluorescence signal is amplified.

"Bioorthogonal reaction" is a chemical reaction that occurs in a physiological environment, and refers to a chemical reaction that occurs selectively with a substance introduced from outside without causing a reaction with in vivo intrinsic molecules.

"Fluorescence quencher" refers to a chemical substance that is connected to a phosphor to reduce a fluorescence signal, and exhausts the excited energy absorbed from the phosphor through a process such as heat emission rather than in the form of light.

The conventional phosphor-tetrazine bichromophore type has a structural form in which the π-electron sharing between the phosphor and the quencher is cut off, and it was the way in which the energy of the fluorescent molecule was transferred into tetrazine through dipole-dipole exchange or electron interchange manner. Therefore, it was not possible to prevent the decrease in fluorescence amplification efficiency in a long wavelength range (>600 nm), which is known to have an excellent light transmittance in vivo.

On the other hand, the phosphor-tetrazine monochromophore type of the present invention uses a compound designed to share the π-electrons of the two molecules in the form of a single molecule by connecting the phosphor and the quencher in one adjacent plane, and unlike the bichromophore type, there is no distinction between an energy donor and acceptor, and energy absorbed in a form other than light is exhausted by emitting the excited energy through the non-magnetic radiation transition of the quencher. Due to these properties, the monochromophore type can obtain high fluorescence amplification efficiency even in a long wavelength range.

The compound of the present invention may be used as a fluorogenic probe, and in particular, may be used as a multiplex imaging fluorogenic probe.

In addition, the compound of the present invention may be used as a fluorogenic probe through a bioorthogonal reaction in vivo.

Hereinafter, examples and comparative examples of the present invention will be described. However, the following examples are only embodiments of the present invention, and the present invention is not limited to the following examples.

Example 1

Preparation of Formula 2 (tert-butyl (3-(7-(6-methyl-1,2,4,5-tetrazin-3-yl)-3-oxo-9-phenyl-1,3-dihydro-2H-pyrrolo[3,4-b]indolizin-2-yl)propyl)carbamate)

[Formula 2]

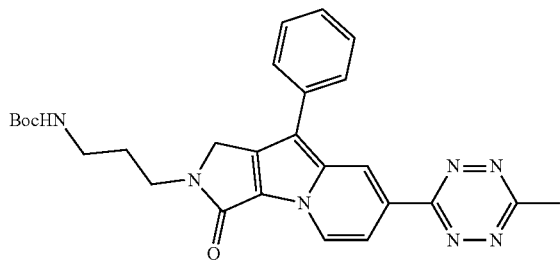

10 ml of a mixed solution of tert-butyl (3-(7-cyano-3-oxo-9-phenyl-1H-pyrrolo[3,4-b]indolizin-2(3H)-yl)propyl)carbamate (64.5 mg, 150 mol), acetonitrile (391 µL, 7.49 mmol), zinc trifluoromethanesulfonate (27.2 mg, 74.9 µmol) and hydrazine monohydrate (728 µL, 15.0 mmol) was added to a microwave reaction vial, and was magnetically stirred for 30 minutes under a microwave at 80° C. (100 W). After cooling to room temperature, sodium nitrite was added to 1 mL of water, and then 1N HCl was slowly added until the pH reached 3. Then, the resulting residue was washed with a saturated NaHCO$_3$ aqueous solution, and then extracted with CH$_2$Cl$_2$, and dried over anhydrous Na$_2$SO$_4$ and then concentrated. After concentration, the crude product was purified by HPLC using a linear gradient of methanol (1-4%) in CH$_2$Cl$_2$ at a flow rate of 5 ml/min to obtain 16.7 mg of Formula 2 as a red solid.

$^1$H NMR (400 MHz, CDCl$_3$) 9.16 (s, 1H), 8.69 (d, J=7.4 Hz, 1H), 7.87 (d, J=7.4 Hz, 1H), 7.59 (d, J=7.4 Hz, 2H), 7.50 (t, J=7.6 Hz, 2H), 7.35 (t, J=7.3 Hz, 1H), 5.39 (br s, 1H, NH), 4.53 (s, 2H), 3.70 (t, J=6.3 Hz, 2H), 3.20 (m, 2H), 3.10 (s, 3H), 1.86 (quin, J=6.3 Hz, 2H), 1.44 (s, 9H); $^{13}$C NMR (100 MHz, CDCl$_3$) 167.0, 163.2, 162.0, 156.2, 135.6, 135.2, 133.6, 129.4, 127.6, 127.0, 125.6, 124.2, 122.8, 119.8, 113.8, 109.2, 79.2, 46.8, 40.2, 37.4, 28.9, 28.6, 21.3; HRMS (ESI) m/z calcd for C$_{27}$H$_{29}$N$_7$NaO$_3$ [M+Na]$^+$: 522.2224, found: 522.2225.

Example 2

Preparation of Formula 3 (tert-butyl (3-(9-(4-methoxyphenyl)-7-(6-methyl-1,2,4,5-tetrazin-3-yl)-3-oxo-1,3-dihydro-2H-pyrrolo[3,4-b]indolizin-2-yl)propyl)carbamate)

[Formula 3]

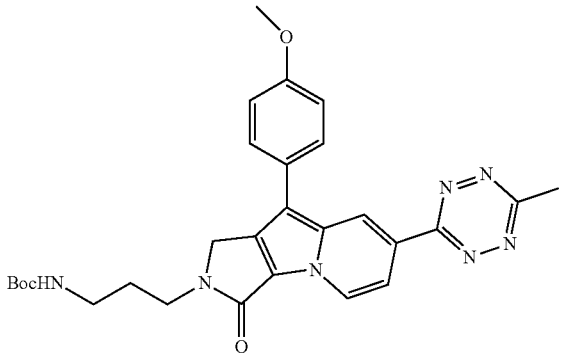

tert-butyl (3-(7-cyano-9-(4-methoxyphenyl)-3-oxo-1H-pyrrolo[3,4-b]indolizin-2(3H)-yl)propyl)carbamate (33.4 mg, 72.5 µmol), acetonitrile (190 µL, 3.63 mmol), zinc trifluoromethanesulfonate (13.2 mg, 36.3 µmol) and hydrazine monohydrate (352 µL, 7.25 mmol) were added to a microwave reaction vial, and irradiated under a microwave at 80° C. (100 W) while magnetically stirring for 0.5 hours. After cooling this to room temperature, sodium nitrite (250 mg, 3.63 mmol) was added to 1 mL of water, and 1N HCl was slowly added until the pH reached 3. Then, the resulting residue was washed with saline, and extracted with CH$_2$Cl$_2$, and then dried over anhydrous Na$_2$SO$_4$. After concentration under reduced pressure, the crude product was purified by normal-phase preparative HPLC using a gradient of methanol (1 to 10%) in CH$_2$Cl$_2$ at a flow rate of 5 ml/min to obtain Formula 3 as a red solid (7.0 mg, 18% yield).

$^1$H NMR (400 MHz, CDCl$_3$) 9.12 (s, 1H), 8.69 (d, J=7.4 Hz, 1H), 7.86 (dd, J=7.2, 1.2 Hz, 1H), 7.53 (d, J=8.6 Hz, 2H), 7.05 (d, J=8.6 Hz, 2H), 5.39 (br s, 1H, NH), 4.51 (s, 2H), 3.89 (s, 3H), 3.70 (t, J=6.3 Hz, 2H), 3.19 (q, J=5.9 Hz, 2H), 3.09 (s, 3H), 1.85 (quin, J=6.3 Hz, 2H), 1.43 (s, 9H); $^{13}$C NMR (100 MHz, CDCl$_3$) 166.8, 163.1, 162.0, 158.6, 156.1, 135.3, 134.6, 128.7, 125.9, 125.4, 123.6, 122.5, 119.8, 114.8, 113.6, 108.9, 79.1, 55.4, 46.6, 40.1, 37.2, 28.7, 28.4, 21.2; HRMS (ESI) m/z calcd for C$_{28}$H$_{31}$N$_7$NaO$_4$ [M+Na]$^+$: 552.2330, found: 552.2330.

Example 3

Preparation of Formula 4 (tert-butyl (3-(9-(4-aminophenyl)-7-(6-methyl-1,2,4,5-tetrazin-3-yl)-3-oxo-1,3-dihydro-2H-pyrrolo[3,4-b]indolizin-2-yl)propyl)carbamate)

[Formula 4]

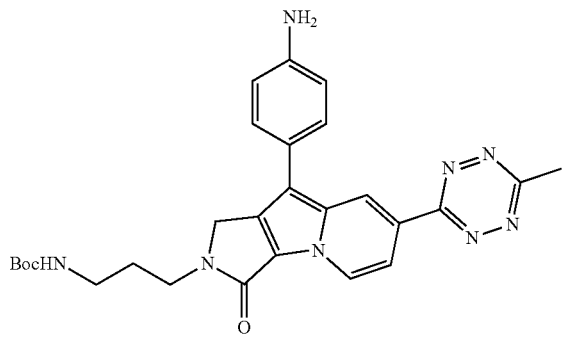

tert-butyl (3-(7-cyano-9-(4-nitrophenyl)-3-oxo-1H-pyrrolo[3,4-b]indolizin-2(3H)-yl)propyl)carbamate (40 mg, 84 μmol), acetonitrile (220 μL, 4.21 mmol), zinc trifluoromethanesulfonate (15.3 mg, 42.1 μmol) and hydrazine monohydrate (409 μL, 8.41 mmol) were added to a microwave reaction vial (10 ml), and irradiated under a microwave at 80° C. (100 W) while magnetically stirring for 1.5 hours. Then, after cooling to room temperature, sodium nitrite (290 mg, 4.21 mmol) was added to 0.5 mL of water, and 1N HCl was slowly added until the pH reached 3. Then, the resulting residue was washed with a saturated $NaHCO_3$ aqueous solution, and extracted with $CH_2Cl_2$, and then dried over anhydrous $Na_2SO_4$ and concentrated. Thereafter, the resulting crude product was purified by normal-phase preparative HPLC using a linear gradient of methanol (0.1-10%) in $CH_2Cl_2$ at a flow rate of 5 ml/min to obtain Formula 4 as a reddish brown solid (2 mg, 5% yield).

$^1$H NMR (400 MHz, $CDCl_3$) 9.13 (s, 1H), 8.67 (d, J=7.4 Hz, 1H), 7.84 (dd, J=7.4, 1.6 Hz, 1H), 7.41 (d, J=8.2 Hz, 2H), 6.83 (d, J=8.6 Hz, 2H), 5.39 (br s, 1H, NH), 4.50 (s, 2H), 3.81 (br s, 2H, $NH_2$), 3.70 (t, J=6.3 Hz, 2H), 3.19 (q, J=6.2 Hz, 2H), 3.09 (s, 3H), 1.84 (quin, J=6.2 Hz, 2H), 1.43 (s, 9H); $^{13}$C NMR (150 MHz, $CDCl_3$) 166.7, 163.2, 162.0, 156.1, 145.5, 135.2, 134.4, 128.7, 125.4, 123.6, 123.3, 122.4, 120.1, 115.8, 114.2, 108.8, 79.1, 46.6, 40.1, 37.3, 28.7, 28.4, 21.2; HRMS (ESI) m/z calcd for $C_{27}H_{30}N_8NaO_3$ [M+Na]$^+$: 537.2333, found: 537.2335.

Example 4

Preparation of Formula 5 (tert-butyl (3-(9-(4-(diethylamino)phenyl)-7-(6-methyl-1,2,4,5-tetrazin-3-yl)-3-oxo-1,3-dihydro-2H-pyrrolo[3,4-b]indolizin-2-yl)propyl)carbamate)

[Formula 5]

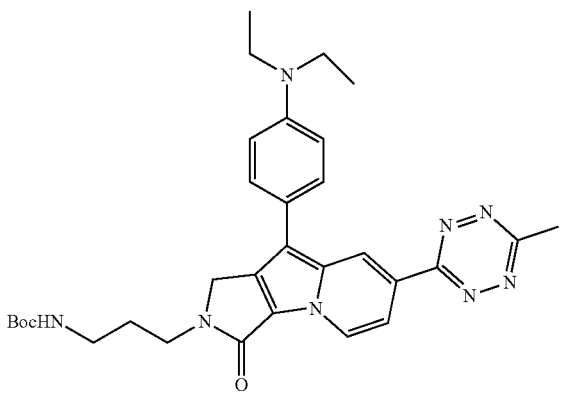

tert-butyl (3-(7-cyano-9-(4-diethylamino)phenyl)-3-oxo-1H-pyrrolo[3,4-b]indolizin-2(3H)-yl)propyl)carbamate (60.2 mg, 120 μmol), acetonitrile (313 μL, 6.00 mmol), zinc trifluoromethanesulfonate (21.8 mg, 60.0 μmol) and hydrazine monohydrate (583 μL, 12.0 mmol) were added to a microwave reaction vial (10 ml), and irradiated under a microwave at 100° C. (40 W) while magnetically stirring for 1.5 hours. Then, after cooling to room temperature, sodium nitrite was added, and 1N HCl was slowly added until the pH reached 3. Then, the resulting residue was washed with a saturated $NaHCO_3$ aqueous solution, and extracted with $CH_2Cl_2$, and dried over anhydrous $Na_2SO_4$ and concentrated. Thereafter, the resulting crude product was purified by silica gel flash column chromatography ($CH_2Cl_2$: EtOAc=8:1) to obtain Formula 5 as a reddish brown solid (11.8 mg, 17.2% yield).

$^1$H NMR (400 MHz, $CD_2Cl_2$) 9.15 (s, 1H), 8.65 (d, J=7.0 Hz, 1H), 7.81 (d, J=7.4 Hz, 1H), 7.48 (d, J=8.6 Hz, 2H), 6.83 (d, J=8.2 Hz, 2H), 5.46 (br s, 1H, NH), 4.51 (s, 2H), 3.67 (t, J=6.3 Hz, 2H), 3.43 (q, J=6.8 Hz, 4H), 3.14 (q, J=6.0 Hz, 2H), 3.05 (s, 3H), 1.81 (quin, J=6.3 Hz, 2H), 1.42 (s, 9H), 1.21 (t, J=7.0 Hz, 6H); $^{13}$C NMR (100 MHz, $CDCl_3$) 166.6, 163.2, 162.1, 156.1, 146.7, 135.0, 134.1, 128.6, 125.3, 122.9, 122.4, 120.4, 120.1, 114.6, 112.2, 108.6, 79.0, 46.7, 44.5, 40.0, 37.2, 28.7, 28.4, 21.2, 12.7; HRMS (ESI) m/z calcd for $C_{31}H_{38}N_8NaO_3$ [M+Na]$^+$: 593.2959, found: 593.2960.

Example 5

Preparation of Formula 6 (3-(4-(3-(7-(6-methyl-1,2,4,5-tetrazin-3-yl)-3-oxo-9-phenyl-1,3-dihydro-2H-pyrrolo[3,4-b]indolizin-2-yl)propyl)piperazin-1-yl)propanoic acid)

[Formula 6]

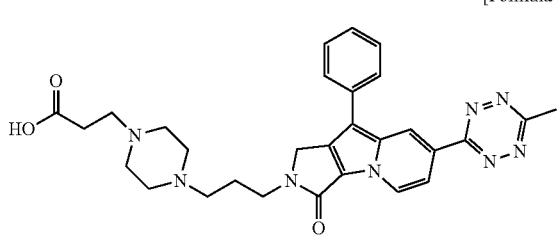

A suspension in which tert-butyl 4-(3-(7-(6-methyl-1,2,4,5-tetrazin-3-yl)-3-oxo-9-phenyl-1H-pyrrolo[3,4]indolizin-2(3H)-yl)propyl)piperazin-1-carboxylate, 3-bromopropanoic acid (4.8 mg, 32 µmol) and N,N-diisopropylethylamine (28 µL, 160 µmol) were dissolved in DMF (160 µL) was stirred at 50° C. for 2 hours. The crude product was directly purified by reverse-phase preparative HPLC using a linear gradient of acetonitrile (5-100%) in water containing 1% TFA to obtain a TFA salt of Compound 6 (5.7 mg, 47% yield).

$^1$H NMR (400 MHz, CDCl$_3$:MeOD-d$_4$=10:1, v/v) 9.15 (s, 1H), 8.67 (d, J=7.4 Hz, 1H), 7.87 (d, J=7.4 Hz, 1H), 7.64 (d, J=7.4 Hz, 2H), 7.52 (t, J=7.6 Hz, 2H), 7.36 (t, J=7.5 Hz, 1H), 4.60 (s, 2H), 3.72 (t, J=6.5 Hz, 2H), 3.31 (br s, 8H), 3.20-3.11 (m, 4H), 3.07 (s, 3H), 2.70 (t, J=6.8 Hz, 2H), 2.18-2.11 (m, 2H); $^{13}$C NMR (100 MHz, CDCl$_3$:MeOD-d$_4$=10:1, v/v) 172.8, 167.5, 163.4, 162.5, 136.2, 136.0, 133.8, 129.6, 127.9, 127.2, 125.9, 124.9, 122.5, 119.9, 114.0, 109.6, 54.9, 52.9, 50.5, 49.8, 47.2, 40.5, 30.1, 24.1, 21.3; HRMS (ESI) m/z calcd for C$_{29}$H$_{33}$N$_8$O$_3$ [M+H]$^+$: 541.2670, found: 541.2674.

Example 6

Preparation of Formula 7 (9-(4-(diethylamino)phenyl)-7-(6-methyl-1,2,4,5-tetrazin-3-yl)-2-(3-(4-methylpiperazin-1-yl)propyl)-1,2-dihydro-3H-pyrrolo[3,4-b]indolizin-3-one)

[Formula 7]

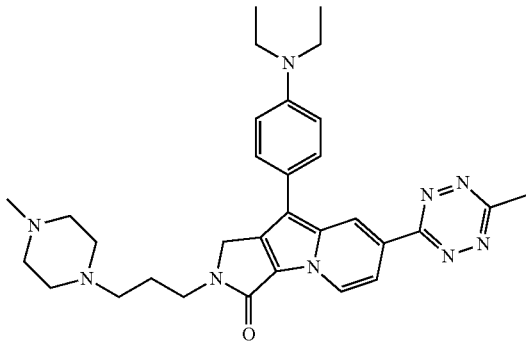

9-(4-(diethylamino)phenyl)-2-(3-(4-methylpiperazin-1-yl)propyl)-3-oxo-2,3-dihydro-1H-pyrrolo[3,4-b]indolizin-7-carbonitrile (15.2 mg, 31.3 µmol), acetonitrile (82 µL, 1.6 mmol), zinc trifluoromethanesulfonate (5.7 mg, 16 µmol) and hydrazine monohydrate (152 µL, 3.13 mmol) were added to a microwave reaction vial (10 ml), and irradiated under a microwave at 100° C. (40 W) while magnetically stirring for 1.5 hours. Then, after cooling to room temperature, sodium nitrite (43.3 mg, 627 µmol) was added to 1 mL of water, and then 1N HCl was slowly added until the pH reached 3. Then, the resulting residue was washed with a saturated NaHCO$_3$ aqueous solution, and extracted with CH$_2$Cl$_2$, and dried over anhydrous Na$_2$SO$_4$ and concentrated. The crude product was purified by reverse-phase preparative HPLC using a linear gradient of acetonitrile (5-100%) in 1% TFA aqueous solution to obtain a TFA salt of Formula 7 (6.5 mg, 31% yield).

$^1$H NMR (400 MHz, CDCl$_3$) 9.17 (s, 1H), 8.66 (d, J=7.5 Hz, 1H), 7.81 (d, J=7.5 Hz, 1H), 7.47 (d, J=8.6 Hz, 2H), 6.81 (d, J=8.6 Hz, 2H), 4.52 (s, 2H), 3.67 (t, J=7.0 Hz, 2H), 3.43 (q, J=7.0 Hz, 4H), 3.07 (s, 3H), 2.47 (m, 10H), 2.28 (s, 3H), 1.90 (quin, J=7.1 Hz, 2H), 1.23 (t, J=7.0 Hz, 6H); $^{13}$C NMR (100 MHz, CDCl$_3$) 166.5, 163.2, 161.6, 146.7, 134.9, 134.1, 128.6, 125.3, 122.9, 122.7, 120.4, 120.2, 114.5, 112.3, 108.5, 55.8, 55.1, 53.2, 46.8, 46.0, 44.5, 41.4, 26.3, 21.1, 12.7; HRMS (ESI) m/z calcd for C$_{31}$H$_{40}$N$_9$O [M+H]$^+$: 554.3350, found: 554.3351.

Comparative Example 1

Preparation of Formula 8 (tert-butyl (3-(7-acetyl-9-(4-(6-methyl-1,2,4,5-tetrazin-3-yl)phenyl)-3-oxo-1,3-dihydro-2H-pyrrolo[3,4-b]indolizin-2-yl)propyl)carbamate)

[Formula 8]

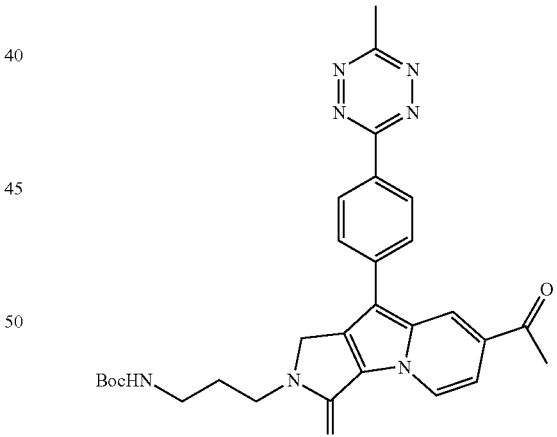

A solution in which tert-butyl (3-(7-acetyl-3-oxo-1H-pyrrolo[3,4-b]indolizin-2(3H)-yl)propyl)carbamate (93.0 mg, 250 µmol), 3-(4-iodophenyl)-6-methyl-1,2,4,5-tetrazine (224 mg, 751 mol), palladium acetate (11.2 mg, 50.0 µmol) and silver acetate (125 mg, 751 µmol) were dissolved in 2.5 mL of N,N-dimethylformamide (DMF) was stirred at 80° C. overnight. Thereafter, the reaction mixture was filtered through celite and concentrated under reduced pressure. The crude product was purified by silica gel flash column chromatography to obtain 7.7 mg of Formula 8 as an orange solid.

¹H NMR (400 MHz, CDCl₃) 8.72 (d, J=8.2 Hz, 2H), 8.62 (d, J=7.4 Hz, 1H), 8.49 (s, 1H), 7.77 (d, J=8.6 Hz, 2H), 7.35 (d, J=7.0 Hz, 1H), 5.32 (br s, 1H, NH), 4.60 (s, 2H), 3.72 (t, J=6.3 Hz, 2H), 3.20 (m, 2H), 3.13 (s, 3H), 2.66 (s, 3H), 1.88 (t, J=6.1 Hz, 2H), 1.43 (s, 9H); ¹³C NMR (100 MHz, CDCl₃) 195.4, 167.2, 163.8, 161.7, 156.1, 137.9, 135.3, 135.0, 130.0, 129.9, 128.8, 127.9, 125.0, 123.2, 120.9, 112.9, 110.1, 79.2, 46.8, 40.2, 37.3, 28.8, 28.4, 26.2, 21.2; HRMS (ESI) m/z calcd for C₂₉H₃₁N₇NaO₄ [M+Na]⁺: 564.2330, found: 564.2331.

Comparative Example 2

Preparation of Formula 9 (tert-butyl (3-(7-acetyl-9-(4-((4-(6-methyl-1,2,4,5-tetrazin-3-yl)benzyl)carbamoyl)phenyl)-3-oxo-1,3-dihydro-2H-pyrrolo[3,4-b]indolizin-2-yl)propyl)carbamate)

[Formula 9]

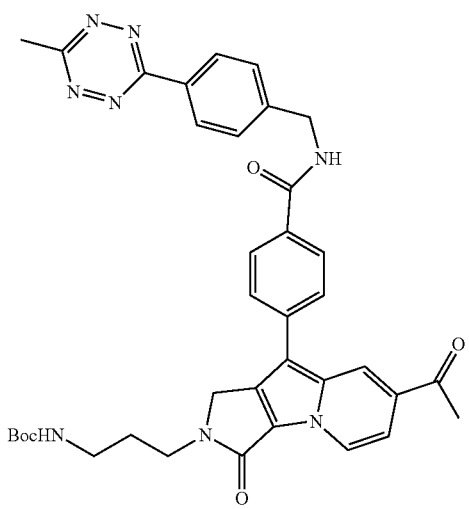

Methyl 4-(7-acetyl-2-(3-((tert-butoxycarbonyl)amino)propyl)-3-oxo-2,3-dihydro-1H-pyrrolo[3,4-b]indolizin-9-yl)benzoate (43.3 mg, 85.7 μmol) and lithium hydroxide monohydrate (10.8 mg, 257 μmol) were added to 0.6 mL of tetrahydrofuran, 0.3 mL of methanol and 0.3 mL of water and stirred at room temperature for 3 hours. Then, the mixture was washed with a saturated NH₄Cl aqueous solution and extracted with CH₂Cl₂, and then dried over anhydrous Na₂SO₄ and concentrated. The resulting N-[(dimethylamino)-1H-1,2,3-triazolo-[4,5-b]pyridin-1-ylmethylene]-N-methylmethanaminium hexafluorophosphate N-oxide (HATU, 65.1 mg, 171 μmol) and N,N-diisopropylethylamine (DIPEA, 74.6 μL, 428 μmol) were dissolved in 1.2 mL of DMF. Thereafter, the solution was stirred at room temperature for 0.5 hours, and then (4-(6-methyl-1,2,4,5-tetrazin-3-yl)phenyl)methanaminium (40.5 mg, 128 μmol) was added to the solution and further stirred at room temperature for 2 hours. The crude product was purified by silica gel flash column chromatography, and then washed several times with EtOAc, and dried in vacuo to obtain 21 mg of Formula 9 as a red solid.

¹H NMR (500 MHz, CD₂Cl₂) 8.59-8.57 (m, 3H), 8.44 (s, 1H), 7.98 (d, J=8.3 Hz, 2H), 7.68 (d, J=8.3 Hz, 2H), 7.63 (d, J=8.3 Hz, 2H), 7.32 (dd, J=7.3, 1.5 Hz, 1H), 6.75 (t, J=5.8 Hz, 1H, NH), 5.36 (br s, 1H, NH), 4.80 (d, J=5.9 Hz, 2H), 4.54 (s, 2H), 3.67 (t, J=6.4 Hz, 2H), 3.10 (m, 2H), 3.07 (s, 3H), 2.60 (s, 3H), 1.81 (quin, J=6.3 Hz, 2H), 1.41 (s, 9H); ¹³C NMR (100 MHz, CDCl₃:MeOD-d₄=10:1, v/v) 196.1, 167.6, 167.3, 163.9, 161.9, 156.6, 143.5, 137.0, 135.4, 135.1, 132.2, 130.8, 129.7, 128.5, 128.34, 128.26, 127.4, 124.9, 122.9, 120.9, 113.1, 110.2, 79.4, 46.8, 43.7, 40.4, 37.5, 28.7, 28.4, 26.3, 21.1; HRMS (ESI) m/z calcd for C₃₇H₃₈N₈NaO₅ [M+Na]⁺: 697.2857, found: 697.2860.

Comparative Example 3

Preparation of Formula 10 (tert-butyl (3-(7-((4-(6-methyl-1,2,4,5-tetrazin-3-yl)benzyl)carbamoyl)-3-oxo-9-phenyl-1,3-dihydro-2H-pyrrolo[3,4-b]indolizin-2-yl)propyl)carbamate)

[Formula 10]

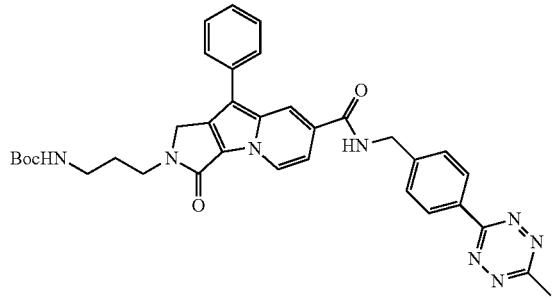

Methyl 2-(3-((tert-butoxycarbonyl)amino)propyl)-3-oxo-9-phenyl-2,3-dihydro-1H-pyrrolo[3,4-b]indolizin-7-carboxylate (39.2 mg, 84.6 μmol), lithium hydroxide monohydrate (10.6 mg, 254 μmol), 0.6 mL of tetrahydrofuran, 0.3 mL of methanol and 0.3 mL of water were mixed and stirred at room temperature for 1 hour. Then, the reaction mixture was washed with a saturated NH₄Cl aqueous solution and extracted with EtOAc, and then dried over anhydrous Na₂SO₄ and concentrated. The resulting product and (4-(6-methyl-1,2,4,5-tetrazin yl)phenyl)methanaminium (40.0 mg, 127 μmol), (1-[bis(dimethylamino)methylene]-1H-1,2,3-triazolo[4,5-b]pyridinium 3-oxidehexafluorophosphate (Hexafluorophosphate Azabenzotriazole Tetramethyl Uronium; hereinafter referred to as HATU) (64.3 mg, 169 μmol) and N,N-diisopropylethylamine (73.7 μL, 423 μmol) were dissolved in 0.9 mL of DMF, and the mixture was stirred at room temperature for 2 hours. The solvent was removed under reduced pressure, and then the crude product was purified by silica gel flash column chromatography to obtain 37.6 mg of Formula 10 as a pink solid.

¹H NMR (500 MHz, CD₂Cl₂) 8.57 (d, J=7.3 Hz, 1H), 8.54 (d, J=8.3 Hz, 2H), 8.34 (s, 1H), 7.60-7.56 (m, 4H), 7.48 (t, J=7.8 Hz, 2H), 7.31 (t, J=7.3 Hz, 2H), 7.12 (dd, J=7.1, 1.7 Hz, 1H), 6.79 (t, J=5.9 Hz, 1H, NH), 5.41 (br s, 1H, NH), 4.76 (d, J=5.9 Hz, 2H), 4.49 (s, 2H), 3.64 (t, J=6.4 Hz, 2H), 3.13-3.10 (m, 2H), 3.06 (s, 3H), 1.79 (quin, J=6.4 Hz, 2H), 1.40 (s, 9H); ¹³C NMR (100 MHz, CDCl₃:MeOD-d₄=10:1, v/v) 167.3, 166.4, 163.9, 162.4, 156.6, 143.6, 135.34, 135.29, 133.5, 130.8, 129.2, 128.5, 128.2, 127.5, 126.8, 126.3, 124.7, 121.5, 119.4, 112.7, 109.7, 79.4, 46.8, 43.8, 40.4, 37.5, 28.7, 28.4, 21.1; HRMS (ESI) m/z calcd for C₃₅H₃₆N₈NaO₄ [M+Na]⁺: 655.2752, found: 655.2755.

Comparative Example 4

Preparation of Formula 11 (N[1]-(3-(7-acetyl-3-oxo-9-phenyl-1,3-dihydro-2H-pyrrolo[3,4-b]indolizin-2-yl)propyl)-N[4]-(4-(6-methyl-1,2,4,5-tetrazin-3-yl)benzyl)succinimide)

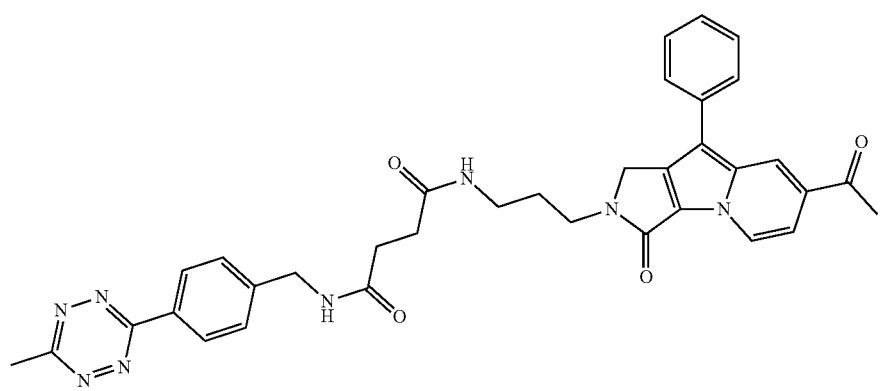

[Formula 11]

A mixture of tert-butyl (3-(7-acetyl-3-oxo-9-phenyl-1H-pyrrolo[3,4-b]indolizin-2(3H)-yl)propyl)carbamate (42 mg, 94 µmol) and 12N HCl (100 µL, 1.2 mmol) was added to 1 mL of $CH_2Cl_2$, and was stirred at room temperature for 2 hours, and then the solvent was concentrated under reduced pressure. The resulting crude solid, succinic anhydride (14.1 mg, 141 µmol) and triethylamine (65.4 µL, 469 µmol) were dissolved in 1 ml of $CH_2Cl_2$. The mixture was stirred at room temperature overnight, and then the crude mixture was directly purified by silica gel flash column chromatography to obtain 36 mg of 4-((3-(7-acetyl-3-oxo-9-phenyl-1H-pyrrolo[3,4-b]indolizin-2(3H)-yl)propyl)amino)-4-oxobutanic acid, the intermediate product, as a yellow solid.

Thereafter, the above intermediate product 4-((3-(7-acetyl-3-oxo-9-phenyl-1H-pyrrolo[3,4-b]indolizin-2(3H)-yl)propyl)amino)-4-oxobutanic acid (33 mg, 74 mol), (4-(6-methyl-1,2,4,5-tetrazin-3-yl)phenyl)methanaminium (35 mg, 110 µmol), HATU (56 mg, 150 µmol) and N,N-diisopropylethylamine (64 µL, 370 µmol) were added to 1 mL of DMF and stirred at room temperature for 2 hours. The crude reaction mixture was directly purified by silica gel flash column chromatography to obtain 23 mg of Formula 11 as an orange solid.

$^1$H NMR (500 MHz, pyridin-$d_5$) 9.41 (t, J=5.9 Hz, 1H, NH), 8.66 (d, J=7.3 Hz, 1H), 8.60 (d, J=7.8 Hz, 2H), 8.57 (s, 1H), 7.77 (d, J=7.3 Hz, 2H), 7.67 (d, J=8.3 Hz, 2H), 7.60-7.57 (m, 2H), 7.44-7.40 (m, 2H), 4.78 (d, J=5.9 Hz, 2H), 4.39 (s, 2H), 3.79 (t, J=7.0 Hz, 2H), 3.63-3.60 (m, 2H), 3.05-3.03 (m, 2H), 2.99-2.95 (m, 5H), 2.61 (s, 3H), 2.06 (quin, J=6.8 Hz, 2H); $^{13}$C NMR (100 MHz, $CDCl_3$:MeOD-$d_4$=10:1, v/v) 196.3, 173.1, 173.0, 167.2, 163.9, 162.2, 143.5, 135.2, 134.9, 133.3, 130.6, 129.43, 129.38, 128.3, 128.1, 127.6, 127.1, 124.7, 122.5, 121.5, 114.4, 109.8, 46.8, 43.1, 40.5, 36.4, 31.73, 31.66, 28.3, 26.1, 21.1; HRMS (ESI) m/z calcd for $C_{35}H_{34}N_8NaO_4$ [M+Na]$^+$: 653.2595, found: 653.2599.

Comparative Example 5

Preparation of Formula 12 (tert-butyl (3-(9-(4-(diethylamino)phenyl)-7-((4-(6-methyl-1,2,4,5-tetrazin-3-yl)benzyl)carbamoyl)-3-oxo-1,3-dihydro-2H-pyrrolo[3,4-b]indolizin-2-yl)propyl)carbamate)

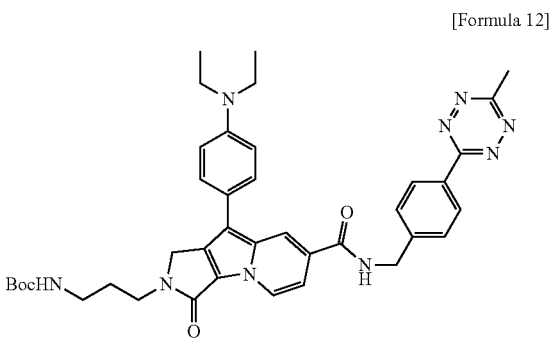 [SMILES: CCN(CC)c1ccc(-c2c3c(n4ccc(C(=O)NCc5ccc(-c6nnc(C)nn6)cc5)cc24)C(=O)N(CCCNC(=O)OC(C)(C)C)C3)cc1]

[Formula 12]

The reaction mixture of methyl 2-(3-((tert-butoxycarbonyl)amino)propyl)-9-(4-(diethylamino)phenyl)-3-oxo-2,3-dihydro-1H-pyrrolo[3,4-b]indolizin-7-carboxylate (26.7 mg, 49.9 µmol), lithium hydroxide monohydrate (6.3 mg, 150 µmol), tetrahydrofuran (THF, 300 µL), methanol (150 µL) and water (150 µL) was stirred at room temperature for 2 hours. Then, the mixture was washed with a saturated $NH_4Cl$ aqueous solution and extracted with EtOAc, and then dried over anhydrous $Na_2SO_4$ and concentrated. The resulting product and (4-(6-methyl-1,2,4,5-tetrazin-3-yl)phenyl)methanaminium (23.6 mg, 74.9 µmol), HATU (38.0 mg, 100 µmol) and N,N-diisopropylethylamine (43.5 µL, 250 µmol) were dissolved in DMF (0.5 mL). The solvent was removed under reduced pressure, and then the crude product was purified by silica gel flash column chromatography (CH$_2$Cl$_2$:methanol=20:1) to obtain Formula 12 as a brown solid (32.9 mg, 93.6% yield).

$^1$H NMR (400 MHz, CDCl$_3$) 8.54 (d, J=8.2 Hz, 2H), 8.48 (d, J=7.4 Hz, 1H), 8.31 (s, 1H), 7.56 (d, J=8.2 Hz, 2H), 7.36 (d, J=9.0 Hz, 2H), 7.04 (d, J=7.0 Hz, 1H), 6.80-6.74 (m, 3H), 5.39 (br s., 1H, NH), 4.77 (d, J=5.9 Hz, 2H), 4.44 (s, 2H), 3.65 (t, J=6.1 Hz, 2H), 3.39 (q, J=7.0 Hz, 4H), 3.15 (d, J=5.9 Hz, 2H), 3.08 (s, 3H), 1.80 (quin, J=6.3 Hz, 2H), 1.42 (s, 9H), 1.19 (t, J=6.8 Hz, 6H); $^{13}$C NMR (100 MHz, CDCl$_3$: MeOD-d$_4$=10:1, v/v) 167.3, 166.7, 164.0, 162.6, 156.7, 146.7, 143.7, 134.8, 134.6, 130.7, 128.6, 128.5, 128.2, 125.2, 124.5, 121.1, 120.3, 119.9, 113.5, 112.5, 109.3, 79.4, 46.9, 44.5, 43.8, 40.4, 37.5, 28.7, 28.4, 21.1, 12.6; HRMS (ESI) m/z calcd for C$_{39}$H$_{46}$N$_9$O$_4$ [M+H]$^+$: 704.3667, found: 704.3669.

Comparative Example 6

Preparation of Formula 13 (N$^1$-(3-(7-acetyl-9-(4-(diethylamino)phenyl)-3-oxo-1,3-dihydro-2H-pyrrolo[3,4-b]indolizin-2-yl)propyl)-N$^4$-(4-(6-methyl-1,2,4,5-tetrazin-3-yl)benzyl)succinimide)

A suspension in which tert-butyl (3-(7-acetyl-9-(4-(diethylamino)phenyl)-3-oxo-1H-pyrrolo[3,4-b]indolizin-2(3H)-yl)propyl)carbamate (45 mg, 87 μmol) and TFA (200 μL, 2.61 mmol) were added to 0.9 mL of CH$_2$Cl$_2$ was stirred at room temperature for 3 hours. Then, the resulting residue was washed with a saturated NaHCO$_3$ aqueous solution and extracted with CH$_2$Cl$_2$, and then dried over anhydrous Na$_2$SO$_4$ and concentrated. The resulting solid, succinic anhydride (13.0 mg, 130 μmol) and triethylamine (60.5 μL, 433 μmol) were dissolved in CH$_2$Cl$_2$ (900 μL). Thereafter, the mixture was stirred at room temperature for 1 hour, and the crude reaction mixture was directly purified by silica gel flash column chromatography (CH$_2$Cl$_2$:methanol=1:1 containing acetic acid 10:1) to obtain the intermediate product as a white solid (35.3 mg, 78.5% yield).

A suspension in which the intermediate product (26 mg, 50 μmol), (4-(6-methyl-1,2,4,5-tetrazin-3-yl)phenyl)methanaminium (23.7 mg, 75.2 μmol), HATU (38.1 mg, 100 μmol) and N,N-diisopropylethylamine (43.7 μL, 251 μmol) were dissolved in DMF (500 μL) was stirred at room temperature for 2 hours. Then, the solvent was removed under reduced pressure, and the crude product was purified by silica gel flash column chromatography (CH$_2$Cl$_2$:methanol=20:1) to obtain Formula 13 as a red solid (26 mg, 74% yield).

$^1$H NMR (400 MHz, CDCl$_3$) 8.45-8.37 (m, 2H), 8.37 (s, 1H), 7.45 (d, J=8.2 Hz, 2H), 7.36 (d, J=8.6 Hz, 2H), 7.24 (d, J=7.0 Hz, 1H), 7.03-6.99 (m, 2H), 6.79 (d, J=8.6 Hz, 2H), 4.55 (d, J=5.9 Hz, 2H), 4.44 (s, 2H), 3.64 (t, J=6.1 Hz, 2H), 3.43 (q, J=7.0 Hz, 4H), 3.29 (q, J=5.6 Hz, 2H), 3.04 (s, 3H), 2.67 (m, 4H), 2.61 (s, 3H), 1.84-1.78 (m, 2H), 1.23 (t, J=7.0 Hz, 6H); $^{13}$C NMR (100 MHz, CDCl$_3$) 195.5, 172.4, 172.3, 167.1, 163.7, 162.2, 146.7, 143.4, 134.1, 133.9, 130.6, 128.54, 128.46, 128.2, 127.9, 124.3, 122.04, 121.99, 119.8, 115.0, 112.2, 109.2, 46.7, 44.4, 43.2, 39.9, 35.8, 32.0, 28.3, 26.0, 21.1, 12.7; HRMS (ESI) m/z calcd for C$_{39}$H$_{43}$N$_9$NaO$_4$ [M+Na]$^+$: 724.3330, found: 724.3333.

[Formula 13]

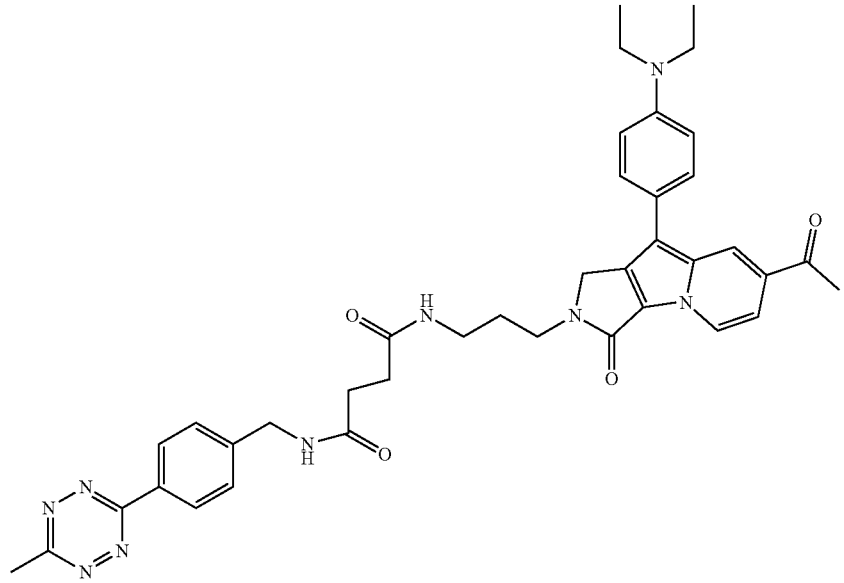

Test Example 1

Change in Absorption Properties According to Reaction of Compound and TCO

In this test, the absorption spectrum was measured with a UV-VIS spectrophotometer UV-1650PC (Shimadzu), and the emission spectrum and motion data were measured using a Cary Eclipse Fluorescence spectrophotometer (Varian Associates), and the absolute quantum yield was measured with a QE-2000 (Otsuka Electronics).

Figure 2:
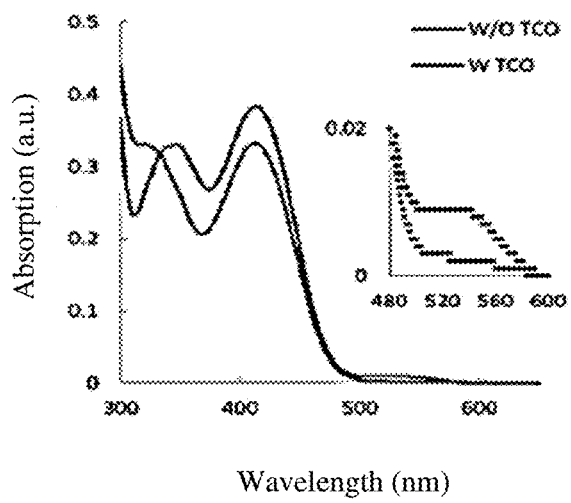
FIG. 2 shows the change in absorbance before and after the reaction between the compounds of Comparative Examples 1 to 4 and TCO.
Figure 2:
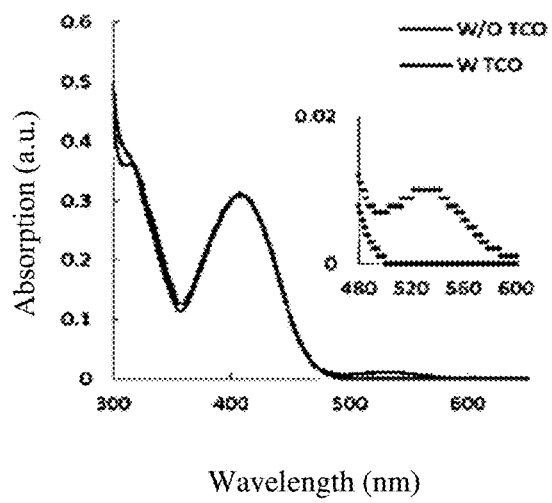
Figure 2:
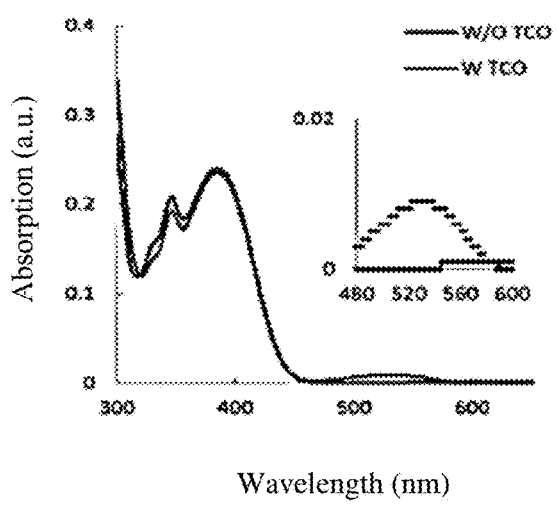
Figure 2:
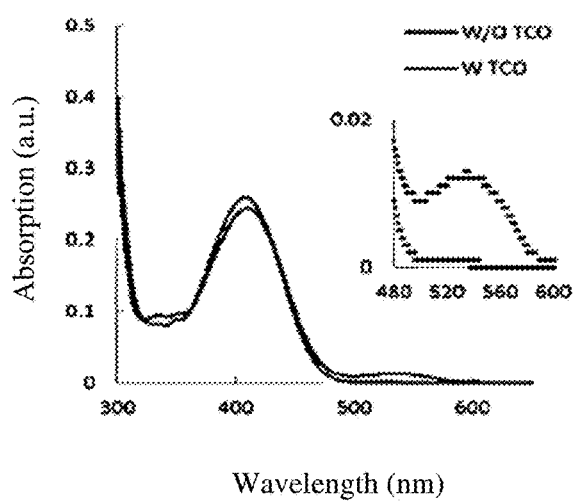

In order to confirm whether it affects the electrical orthogonality of indolizine and tetrazine according to the chemical structure of each compound, the absorption spectrum of each compound before and after bioorthogonal reaction with (E)-cyclooct-4-enol ("TCO") was confirmed, and the results are shown in FIGS. 1 and 2.

The electrical orthogonality can be confirmed by analyzing the change in absorption peak after the reaction with TCO. If indolizine and tetrazine are in two independent and electronically de-coupled states, after the cyclization reaction of the compound and TCO, the absorption peaks around 500-550 nm due to the absorption of tetrazine disappear and the remaining absorption peaks will be maintained the same.

On the other hand, if indolizine and tetrazine are strongly bound to act as a single chromophore, the cyclization reaction with TCO shifts the absorption spectrum toward a short wavelength as a whole due to a decrease in the π-conjugation length.

As shown in FIG. 1, before the TCO treatment, the compounds of Examples 1 to 4 had absorption peaks of about 400-420 nm, but absorption peaks of about 500-550 nm were not observed. Since the tetrazine derivative generally exhibits a distinct absorption peak around 500-550 nm, it can be seen that in the compounds of Examples 1 to 4, the bonding state between indolizine and tetrazine is strong.

In addition, after the TCO treatment, it was confirmed that in the compounds of Examples 1 to 4, the absorption peaks shifted from 415 nm to 386 nm toward a short wavelength as a whole. Therefore, it can be seen that in the compounds of Examples 1 to 4, indolizine and tetrazine have a strong electronic bonding state.

On the other hand, as shown in FIG. 2, before the TCO treatment, it was confirmed that the compounds of Comparative Examples 1 to 4 had two different absorption peaks at about 400-420 nm and 500-550 nm.

After the TCO treatment, in the compounds of Comparative Examples 1 to 4, the absorption peak around 500-550 nm due to the absorption of tetrazine disappeared and the remaining peaks were maintained the same. Therefore, it can be seen that in the compounds of Comparative Examples 1 to 4, indolizine and tetrazine do not have a strong electronic bonding state.

Test Example 2

Change in Emission Properties According to Reaction of Compound and TCO

The emission spectrum was compared when the maximum fluorescence intensity was reached before and after the reaction of the compound and TCO, and changes in fluorescence of the compounds of Examples 1 to 4 and Comparative Examples 1 to 4 were observed, and the results are shown in Table 1 below.

TABLE 1

| No. | $\Phi_{off}$ | $K_2$ $(m^{-1}s^{-1})$ | $\lambda_{ex}$ (nm) | $\lambda_{em}$ (nm) | $\Phi_{on}$ | fluorescence amplification rate (on/off) |
|---|---|---|---|---|---|---|
| Example 1 | 0.002 | 24 | 375 | 484 | 0.683 | >1,000 |
| Example 2 | 0.001 | 23 | 383 | 505 | 0.485 | >1,000 |
| Example 3 | 0.002 | 22 | 390 | 562 | 0.064 | >600 |
| Example 4 | 0.001 | 22 | 401 | 581 | 0.045 | >600 |
| Comparative Example 1 | 0.011 | 21 | 416 | 532 | 0.168 | 20 |
| Comparative Example 2 | 0.042 | 15 | 401 | 522 | 0.583 | 14 |
| Comparative Example 3 | 0.012 | 15 | 375 | 493 | 0.616 | 67 |
| Comparative Example 4 | 0.017 | 8.5 | 401 | 530 | 0.325 | 24 |

$\Phi_{off}$ and $\Phi_{on}$ absolute quantum yield before and after the reaction with TCO, respectively
$K_2$ second rate constant value measured at 20° C.
$\lambda_{ex}$ largest excitation maxima at a given maximum emission wavelength
$\lambda_{em}$ maximum emission wavelength As shown in Table 1 above, the compounds of Examples 1 to 4 exhibited fluorescence property of complete quenching (quantum yield: 0.1 to 0.2%) before the reaction with TCO, and the compounds of Comparative Examples 1 to 4 exhibited the residual fluorescence property (quantum yield: at most 4%) before the reaction with TCO.

In addition, it was confirmed that in the compounds of Comparative Examples 1 to 4, before and after the reaction, the fluorescence signal was amplified by about 10 to 70 times, and in the compounds of Examples 1 and 2, the fluorescence signal was amplified by 1,000 times or more, and in the compounds of Examples 3 and 4, the fluorescence signal was amplified by 600 times or more.

As a result, it can be seen that the compounds of Examples 1 to 4 having a strong electron bond have a complete quenching state before the reaction with TCO, but the fluorescence signal is amplified by 600 to 1000 times or more after the reaction with TCO.

Test Example 3

Test of Fluorescence Amplification According to Substituent

In the compound of Formula 1 below, in order to confirm the influence of substitution of the electron donating group at the $R_1$ position on the fluorescence amplification, a diethylamino group as an electron donating group was introduced at the $R_1$ position of Comparative Examples 3 and 4 to prepare Comparative Examples 5 and 6.

[Formula 1]

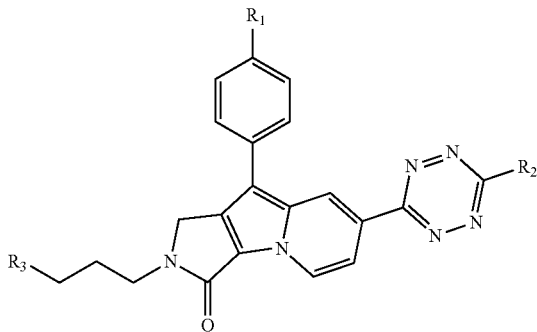

Figure 3:
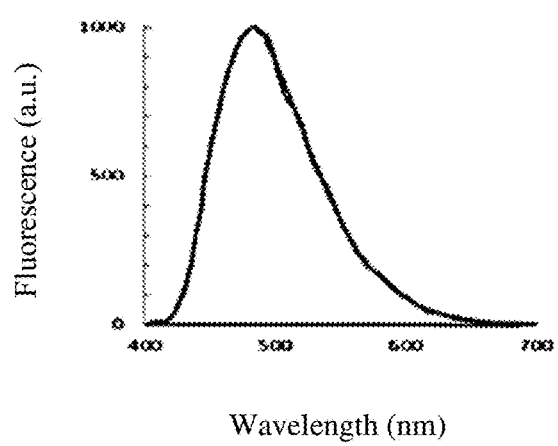
FIG. 3 shows the fluorescence intensity before and after the reaction between the compounds of Examples 1 to 4 and TCO.
Figure 3:
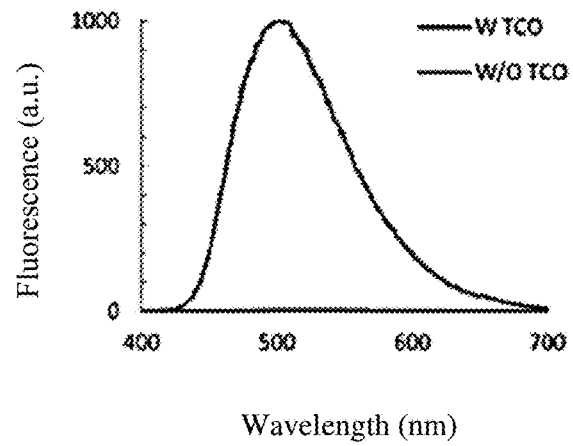
Figure 3:
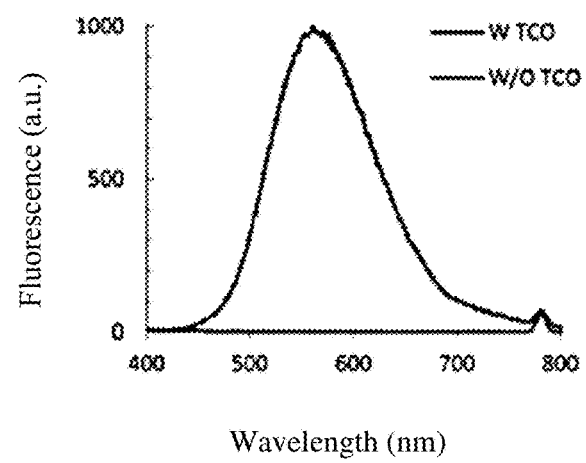
Figure 3:
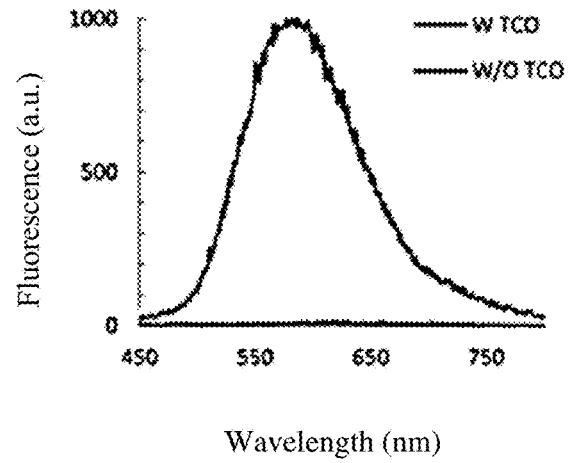
Figure 4:
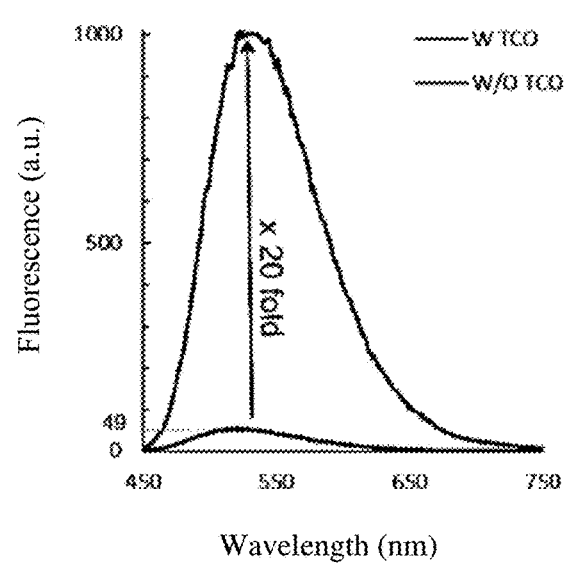
FIG. 4 shows the change in fluorescence intensity before and after the reaction between the compounds of Comparative Examples 1 to 4 and TCO.
Figure 4:
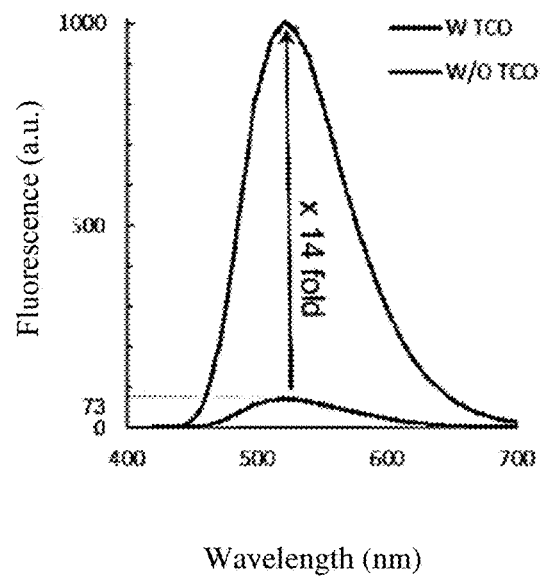
Figure 4:
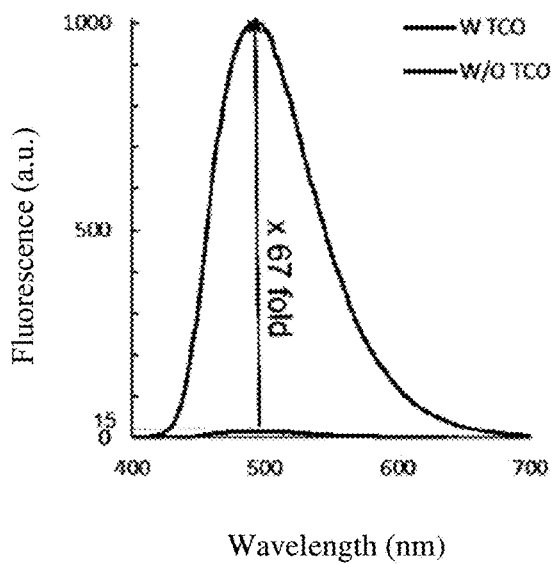
Figure 4:
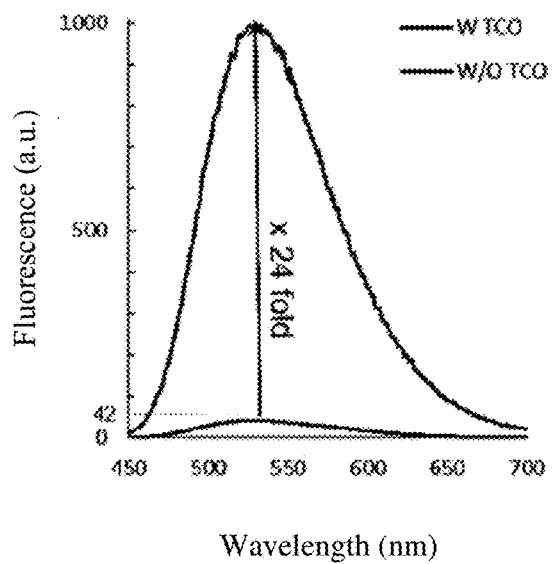

The emission spectrum was compared when the maximum fluorescence intensity was reached before and after the reaction of the compound and TCO, and changes in fluorescence of the compounds of Examples 1 and 4 and Comparative Examples 3 to 6 were observed, and the results are shown in Table 2 below, FIGS. 3 and 4.

TABLE 2

| No. | $\Phi_{off}$ | $K_2$ $(m^{-1}s^{-1})$ | $\lambda_{ex}$ (nm) | $\lambda_{em}$ (nm) | $\Phi_{on}$ | fluorescence amplification rate (on/off) |
|---|---|---|---|---|---|---|
| Example 1 | 0.002 | 24 | 375 | 484 | 0.683 | >1,000 |
| Example 4 | 0.001 | 22 | 401 | 581 | 0.045 | >600 |
| Comparative Example 3 | 0.012 | 15 | 375 | 493 | 0.616 | 67 |
| Comparative Example 4 | 0.017 | 8.5 | 401 | 530 | 0.325 | 24 |

TABLE 2-continued

| No. | $\Phi_{off}$ | $K_2$ $(m^{-1}s^{-1})$ | $\lambda_{ex}$ (nm) | $\lambda_{em}$ (nm) | $\Phi_{on}$ | fluorescence amplification rate (on/off) |
|---|---|---|---|---|---|---|
| Comparative Example 5 | 0.005 | 15 | 418 | 608 | 0.016 | 30 |
| Comparative Example 6 | 0.013 | 1.2 | 438 | 625 | 0.028 | 3 |

$\Phi_{off}$ and $\Phi_{on}$ absolute quantum yield before and after the reaction with TCO, respectively
$K_2$ second rate constant value measured at 20° C.
$\lambda_{ex}$ largest excitation maxima at a given maximum emission wavelength
$\lambda_{em}$ maximum emission wavelength As shown in Table 2 above, it was confirmed that after the reaction with TCO, in the compounds of Comparative Examples 5 and 6, the fluorescence signal amplification efficiency was significantly reduced compared to Comparative Examples 4 and 5.

Therefore, it can be seen that the compounds of Examples 1 and 4 having the structure of the phosphor-quencher monochromophore type have an excellent fluorescence signal amplification efficiency even in a long wavelength range, which is independent of the electron donating group at the $R_1$ position.

Test Example 4

Experiment to Confirm Bio-Applicability of Compound (Microtubule)

Since the compound of the present invention has high fluorescence amplification efficiency even in a long wavelength range, it was confirmed by the following method whether it has utility as a multiplex imaging probe capable of simultaneously confirming various colors.

The fluorescence imaging test was performed using a DeltaVision Elite imaging system of GE Healthcare, and an Olympus IX-71 microscope was used.

For in vivo use, the compounds of Examples 5 and 6 were prepared by introducing water-soluble substituents such as piperazine and carboxyl groups at the $R_3$ position of Formula 1 below.

[Formula 1]

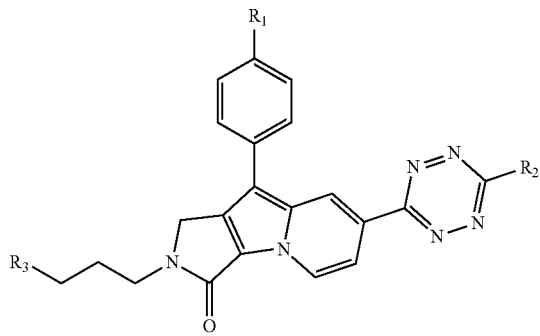

Docetaxel-TCO conjugate (Dox-TCO) was used for fluorescence bio-imaging of microtubule. HeLa human cervical cancer cells were fixed, and cultured with Dox-TCO for 1 hour, and then washed with PBS.

As soon as the compound of Example 5 or Example 6 was added to the cells, a bright fluorescence signal was generated, and the intracellular fluorescence image was observed to be similar to a typical spindle structure of microtubules.

On the other hand, in the group not treated with the compound of Example 5 or 6, it was confirmed that there was a negligible background signal inside the cells and no background signal outside the cells.

In addition, it was confirmed that it was microtubule specific staining by observing that the result of an additional immunofluorescence test using an α-tubulin antibody was consistent with the position of the fluorescence signal of Example 5 or Example 6.

Test Example 5

Experiment to Confirm Bio-Applicability of Compound (Mitochondria)

In order to confirm the fluorescence imaging of mitochondria in living cells, it was tested by the following method.

HeLa cells were incubated for 1 hour in the presence or absence of triphenylphosphonium (TPP)-TCO, and then HeLa cells were washed and treated with the compound of Example 5 or Example 6.

In the case of no treatment with TPP-TCO, no specific staining or background signal of mitochondria was observed.

On the other hand, in the case of treatment with TPP-TCO and the compound of Example 5 or TPP-TCO and the compound of Example 6, a clear fluorescence mitochondria image was observed, and the fluorescence expression intensity was observed to be 0 in the extracellular region.

In addition, in order to confirm the selectivity of TPP-TCO and Example 5, and TPP-TCO and Example 6 for mitochondria, HeLa cells were treated with MitoTracker Deep Red, a mitochondria coloring dye, As a result, it was observed that the position of the fluorescence signal of MitoTracker Deep Red was consistent with that of Example 5 or Example 6.

As a result, it can be seen that through the compound of the present invention, fluorescence signals inside and outside cells can be clearly obtained without a washing step and a cell fixation step for removing the fluorogenic probe. In addition, it can be seen that the compound of the present invention can secure excellent fluorescence image in various fluorescence wavelength ranges, and can be utilized as multiplex imaging.

The invention claimed is:

1. A compound represented by Formula 1 below:

[Formula 1]

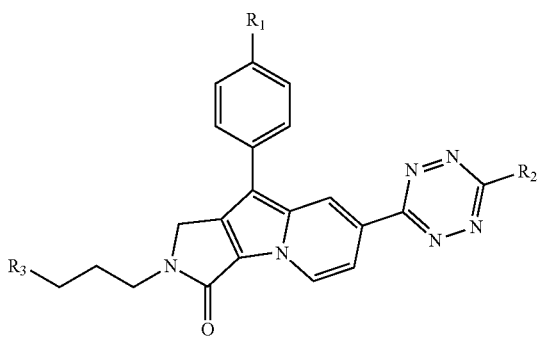

in which,
$R_1$ is hydrogen, $C_1$-$C_6$ alkoxy, hydroxy or $NR_4R_5$ (wherein, $R_4$ and $R_5$ are each independently hydrogen, a $C_1$-$C_6$ alkyl group or a $C_3$-$C_8$ cycloalkyl group), R$_2$ is hydrogen, a C$_1$-C$_6$ alkyl, C$_6$-C$_{20}$ aryl or C$_4$-C$_{20}$ heteroaryl group, and R$_3$ is hydrogen, hydroxy, an alcohol protected by tri-isopropylsilyl (TIPS), a C$_3$-C$_8$ heterocyclic or amine group, wherein the heterocyclic or amine group may or may not be substituted with C$_1$-C$_6$ alkyl; a carboxylC$_1$-C$_6$alkyl or tert-butyloxycarbonyl group (Boc group).

2. The compound according to claim 1,
wherein R$_1$ is hydrogen, C$_1$-C$_6$ alkoxy, or NR$_4$R$_5$ (wherein, R$_4$ and R$_5$ are each independently hydrogen or a C$_1$-C$_6$ alkyl group), R$_2$ is hydrogen or C$_1$-C$_6$ alkyl, and R$_3$ is hydrogen, a C$_3$-C$_8$ heterocyclic or amine group, and wherein the heterocyclic or amine group may or may not be substituted with C$_1$-C$_6$ alkyl; a carboxylC$_1$-C$_6$alkyl or tert-butyloxycarbonyl group (Boc group).

3. The compound according to claim 2, wherein R$_2$ is C$_1$-C$_6$ alkyl.

4. The compound according to claim 1, selected from the group consisting of compounds of Formulae 2 to 7 below:

[Formula 2]

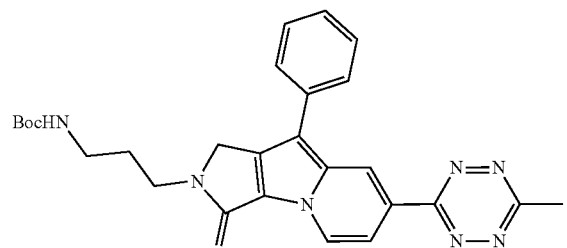

[wherein, Boc is a tert-butyloxycarbonyl group]

[Formula 3]

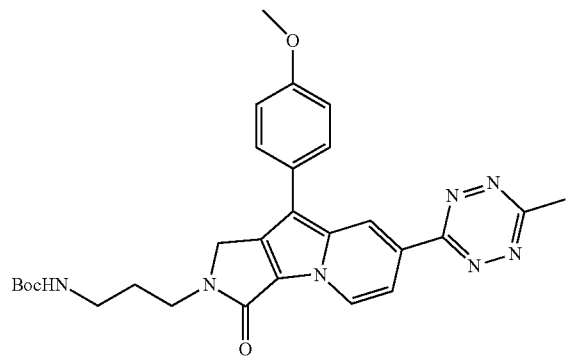

[Formula 4]

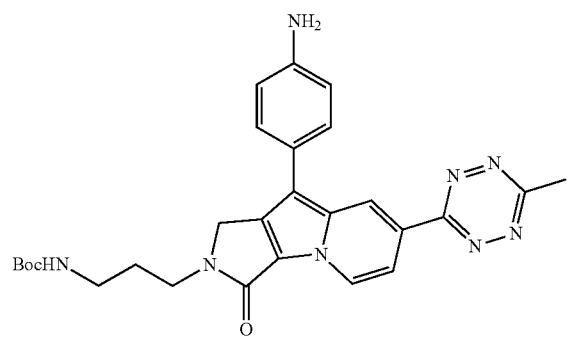

[Formula 5]

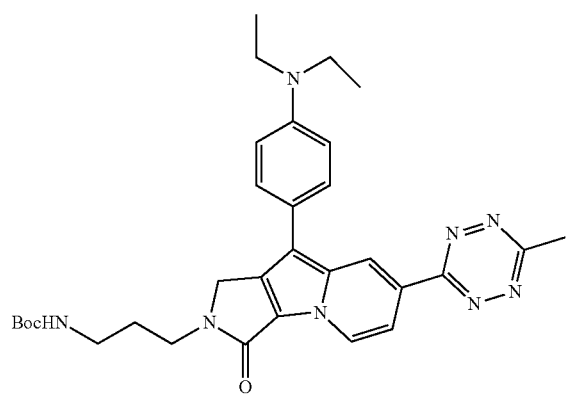

[Formula 6]

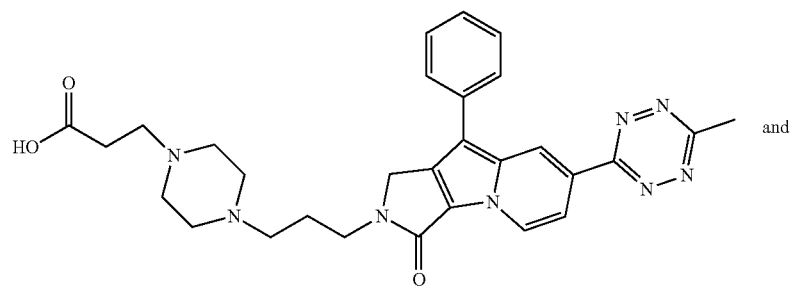

and

-continued
[Formula 7]
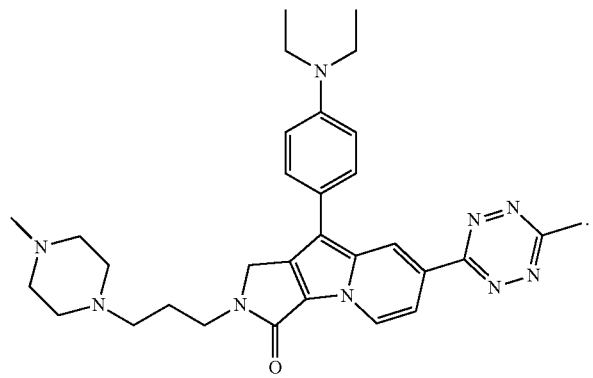
5. A fluorogenic probe comprising the compound according to claim 1.
6. The fluorogenic probe according to claim 5, wherein the compound reacts with a target substance via a bioorthogonal reaction in vivo.
7. The fluorogenic probe according to claim 6, wherein the fluorogenic probe is implemented as a multiplex imaging fluorogenic probe.
* * * * *